(12) United States Patent
Merkel et al.

(10) Patent No.: US 9,950,973 B2
(45) Date of Patent: Apr. 24, 2018

(54) AZEOTROPIC OR AZEOTROPE-LIKE COMPOSITIONS OF 1,3-DICHLORO-3,3-DIFLUOROPROP-1-ENE (HCFO-1232ZD) AND HYDROGEN FLUORIDE (HF)

(71) Applicant: Honeywell International Inc., Morris Plains, NJ (US)

(72) Inventors: Daniel C. Merkel, West Seneca, NY (US); Konstantin A. Pokrovski, Orchard Park, NY (US); Hsueh Sung Tung, Getzville, NY (US); Haiyou Wang, Amherst, NY (US); Ryan J. Hulse, Getzville, NY (US); Hang T. Pham, Amherst, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/252,544

(22) Filed: Aug. 31, 2016

(65) Prior Publication Data

US 2018/0057430 A1 Mar. 1, 2018

(51) Int. Cl.
*C07C 21/18* (2006.01)
*C07C 17/25* (2006.01)
*C07C 17/20* (2006.01)
*C07C 17/04* (2006.01)

(52) U.S. Cl.
CPC .......... *C07C 17/206* (2013.01); *C07C 17/04* (2013.01); *C07C 17/25* (2013.01); *C07C 21/18* (2013.01)

(58) Field of Classification Search
CPC ................................ C07C 21/18; C07C 21/04
See application file for complete search history.

(56) References Cited

U.S. PATENT DOCUMENTS

| | | | |
|---|---|---|---|
| 5,763,706 A | 6/1998 | Tung et al. | |
| 6,013,846 A | 1/2000 | Wismer et al. | |
| 6,365,566 B1 | 4/2002 | Bogdan et al. | |
| 6,475,971 B2 | 11/2002 | Pham et al. | |
| 6,638,987 B2 | 10/2003 | Bogdan et al. | |
| 6,689,924 B1 * | 2/2004 | Thenappan | C07C 17/00 526/906 |
| 6,844,475 B1 | 1/2005 | Tung et al. | |
| 7,964,759 B2 | 6/2011 | Ishihara et al. | |
| 8,008,243 B2 | 8/2011 | Tung et al. | |

(Continued)

FOREIGN PATENT DOCUMENTS

| | | | |
|---|---|---|---|
| WO | 9707052 A1 | 2/1997 | |
| WO | WO 2013161692 A1 * | 10/2013 | C07C 17/21 |

(Continued)

OTHER PUBLICATIONS

Okamoto, S. et al. WO2016009946A1, Jan. 2016, pp. 1-9; English translation.*

(Continued)

*Primary Examiner* — Medhanit W Bahta
(74) *Attorney, Agent, or Firm* — Faegre Baker Daniels LLP

(57) ABSTRACT

Azeotropic or azeotrope-like mixtures of 1,3-dichloro-3,3-difluoroprop-1-ene (HCFO-1232zd) and hydrogen fluoride (HF). Such compositions are useful as a feed stock or intermediate in the production of 1,1,1,3,3-pentafluoropropane (HFC-245fa), 1-chloro-3,3,3-trifluoropropene (HCFO-1233zd), and 1,3,3,3-tetrafluoropropene (HFO-1234ze).

13 Claims, 1 Drawing Sheet

(56) References Cited

U.S. PATENT DOCUMENTS

| | | |
|---|---|---|
| 8,114,308 B2 | 2/2012 | Merkel et al. |
| 8,426,659 B2 | 4/2013 | Holtcamp et al. |
| 8,519,200 B1 | 8/2013 | Merkel et al. |
| 8,546,624 B2 | 10/2013 | Pham et al. |
| 8,747,691 B2 | 6/2014 | Hulse et al. |
| 8,791,309 B2 | 7/2014 | Zhai et al. |
| 8,951,431 B2 | 2/2015 | Hulse et al. |
| 9,000,240 B2 | 4/2015 | Cottrell et al. |
| 9,045,386 B2 | 6/2015 | Tung et al. |
| 9,222,177 B2 | 12/2015 | Merkel et al. |
| 9,272,969 B2 | 3/2016 | Merkel et al. |
| 2009/0234165 A1 | 9/2009 | Chiu et al. |
| 2011/0240902 A1 | 10/2011 | Merkel et al. |
| 2013/0221273 A1 | 8/2013 | Merkel et al. |
| 2014/0264154 A1 | 9/2014 | Merkel et al. |
| 2016/0355453 A1* | 12/2016 | Ohkubo ............... B01J 23/6522 |

FOREIGN PATENT DOCUMENTS

| | | | |
|---|---|---|---|
| WO | 2015092211 A1 | 6/2015 | |
| WO | WO 2016009946 A1 * | 1/2016 | ............. C07C 17/25 |

OTHER PUBLICATIONS

Sakyu, F. WO2013/161692A1, Oct. 2013, pp. 1-18; English translation.*

International Search Report and Written Opinion issued in PCT/US2017/046946, dated Oct. 31, 2017, 13 pages.

* cited by examiner

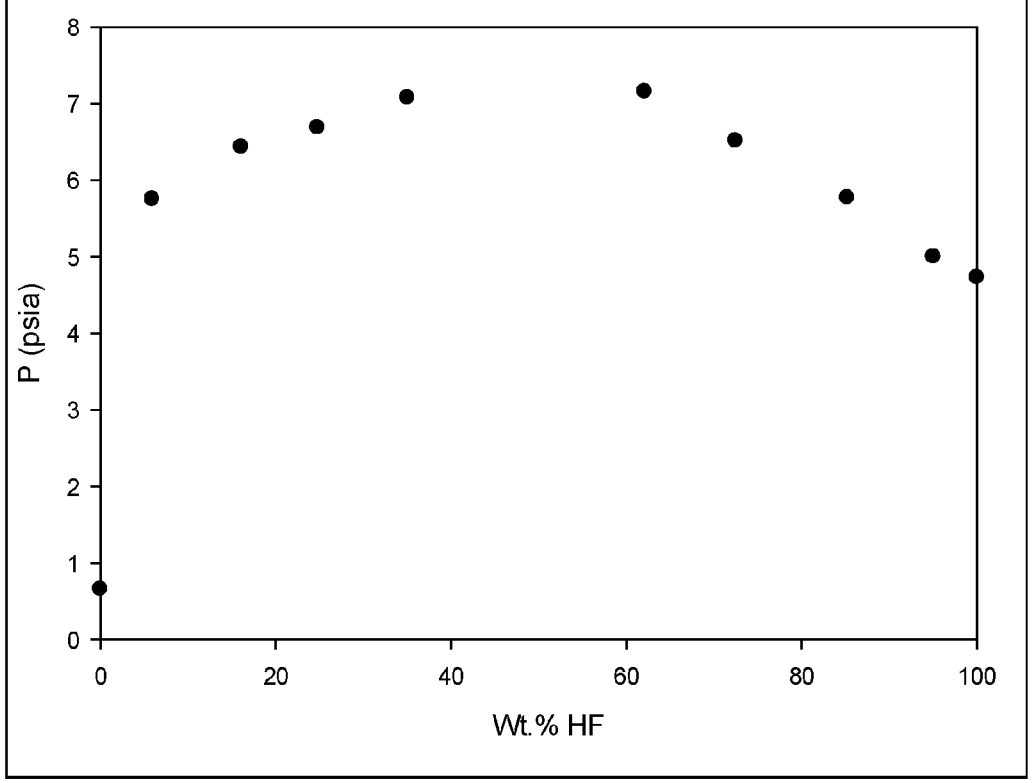

AZEOTROPIC OR AZEOTROPE-LIKE COMPOSITIONS OF 1,3-DICHLORO-3,3-DIFLUOROPROP-1-ENE (HCFO-1232ZD) AND HYDROGEN FLUORIDE (HF)

FIELD OF THE INVENTION

The present invention pertains to azeotropic or azeotrope-like compositions of 1,3-dichloro-3,3-difluoroprop-1-ene (HCFO-1232zd) and hydrogen fluoride (HF).

DESCRIPTION OF THE PRIOR ART

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is considered to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd(E), pure 1233zd(Z), or certain mixtures of the two isomers may be suitable for particular applications as refrigerants, propellants, blowing agents, solvents, or for other uses.

1,3-dichloro-3,3-difluoroprop-1-ene (HCFO-1232zd) can be either a starting material or an intermediate (if starting with a less fluorinated chlorocarbon, e.g. HCC-240fa, 1,1,3,3-tetrachloropropene, 1,3,3,3-tetrachloropropene, and/or 1,1,3,3-tetrachloro-1-fluoropropane) in the production of both 245fa and 1233zd which are well known in the art as described in U.S. Pat. Nos. 5,763,706 and 6,844,475, respectively. Methods of production of 1233zd are also disclosed in U.S. Pat. Nos. 9,045,386 and 9,000,240.

New compositions of, methods of separating and purifying, and uses of, 1,3-dichloro-3,3-difluoroprop-1-ene (HCFO-1232zd) are desired.

SUMMARY OF THE INVENTION

The invention provides a heterogeneous azeotropic or azeotrope-like composition consisting essentially of 1,3-dichloro-3,3-difluoroprop-1-ene (HCFO-1232zd) and hydrogen fluoride (HF).

In another embodiment, composition may consist of 1,3-dichloro-3,3-difluoroprop-1-ene (HCFO-1232zd) and hydrogen fluoride (HF).

In further embodiments, the composition may consist essentially of from about 1 to about 99 wt. % hydrogen fluoride (HF) and from about 1 to about 99 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd). Alternatively, the composition may consist essentially of from about 2 to about 99 wt. % hydrogen fluoride (HF) and from about 1 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd). Still further, the composition may consist essentially of from about 2 to about 80 wt. % hydrogen fluoride (HF) and from about 20 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd). The composition may have a boiling point of about $-10°$ C.$\pm 0.5°$ C. at a pressure of about 7 psia$\pm 1$ psia.

In another form thereof, the present invention provides a method of forming an azeotropic or azeotrope-like composition including forming a blend consisting essentially of from about 1 to about 99 wt. % hydrogen fluoride (HF) and from about 1 to about 99 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd). The composition may consist of 1,3-dichloro-3,3-difluoroprop-1-ene (HCFO-1232zd) and hydrogen fluoride (HF).

In the foregoing method, the forming step may include forming a blend consisting essentially of from about 2 to about 99 wt. % hydrogen fluoride (HF) and from about 1 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd). Alternatively, the forming step may include forming a blend consisting essentially of from about 2 to about 80 wt. % hydrogen fluoride (HF) and from about 20 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd). The composition may have a boiling point of about $-10°$ C.$\pm 0.5°$ C. at a pressure of about 7 psia$\pm 1$ psia.

In a further form thereof, the present invention provides a method for fluorinating an organic compound including the steps of providing an azeotropic or azeotrope-like composition consisting essentially of 1,3-dichloro-3,3-difluoroprop-1-ene (HCFO-1232zd) and hydrogen fluoride (HF); and reacting at least a portion of said 1,3-dichloro-3,3-difluoroprop-1-ene (HCFO-1232zd) in the vapor phase with a fluorinating agent to produce at least one fluorinated organic compound. The reacting step may further include reacting at least a portion of said 1,3-dichloro-3,3-difluoroprop-1-ene (HCFO-1232zd) in the vapor phase with a fluorinating agent to produce 1-chloro-3,3,3-trifluoropropene (HCFO-1233zd), 1,1,1,3,3,-pentafluoropropane (HFC-2451a), and/or 1,3,3,3-tetrafluoropropene (HFO-1234ze).

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

The above mentioned and other features of the invention, and the manner of attaining them, will become more apparent and the invention itself will be better understood by reference to the following description of embodiments of the invention taken in conjunction with the accompanying drawings.

FIG. 1 shows a plot of the vapor pressures of the mixtures formed in Example 2 as measured at −10° C.

Although the drawings represent embodiments of various features and components according to the present disclosure, the drawings are not necessarily to scale and certain features may be exaggerated in order to better illustrate and explain the present disclosure. The exemplification set out herein illustrates an embodiment of the invention, and such exemplification is not to be construed as limiting the scope of the invention in any manner.

DETAILED DESCRIPTION

It has been found that 1,3-dichloro-3,3-difluoroprop-1-ene (also known as, and referred to herein as, HCFO-1232zd or 1232zd) forms heterogeneous azeotropic and azeotrope-like compositions or mixtures with hydrogen fluoride (HF), and the present invention provides heterogeneous azeotropic or azeotrope-like compositions including or comprising 1232zd and HF and, in other embodiments, the composition may consist essentially of 1232zd and HF and, in still further embodiments, the composition may consist of 1232zd and HF.

An azeotrope or azeotrope-like mixture of 1232zd and HF may be used as an intermediate and/or feed stock in the production of 1,1,1,3,3-pentafluoropropane (HFC-245fa), 1-chloro-3,3,3-trifluoropropene (HCFO-1233zd), and 1,3,3,3-tetrafluoropropene (HFO-1234ze), and such compositions are additionally useful as solvent compositions for removing surface oxidation from metals. Further, an azeotrope or azeotrope-like mixture of 1232zd and HF, once formed, may thereafter be separated into its component parts by extraction or distillation techniques. 1232zd has a boiling point of about 74° C. and HF has a boiling point of about 20° C. at standard atmospheric pressure.

The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. Also, as used herein, the term "azeotrope-like" refers to compositions that are strictly azeotropic and/or that generally behave like azeotropic mixtures.

An azeotrope or an azeotrope-like composition is an admixture of two or more different components which, when in liquid form under a given pressure, will boil at a substantially constant temperature, which temperature may be higher or lower than the boiling temperatures of the individual components and which will provide a vapor composition essentially identical to the liquid composition undergoing boiling.

For the purpose of this invention, azeotropic compositions are defined to include azeotrope-like compositions, which is a composition that behaves like an azeotrope, i.e., has constant boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of 1232zd and HF to form an azeotropic or azeotrope-like composition. As used herein, the term "effective amount" is an amount of each component which, when combined with the other component, results in the formation of an azeotrope or azeotrope-like mixture.

The inventive compositions preferably are binary azeotropes which consist essentially of combinations of 1232zd and HF, or consist of combinations of 1232zd and HF. As used herein, the term "consisting essentially of", with respect to the components of an azeotrope-like composition or mixture, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary azeotrope).

As used herein, the terms "heteroazeotrope" and "heterogeneous azeotrope" mean an azeotrope-like composition comprising a vapor phase existing concurrently with two liquid phases.

The invention also provides a method of forming an azeotropic or azeotrope-like composition by combining 1232zd and HF. Any of a wide variety of methods known in the art for combining two or more components to form a composition can be adapted for use in the present methods. For example, 1232zd and HF can be mixed, blended, or otherwise combined by hand and/or by machine, as part of a batch or continuous reaction and/or process, or via combinations of two or more such steps. In one embodiment, when 1,1,1,3,3-pentachloropropane (HCC-240fa) and HF are fed into a reactor, 1232zd is formed as an intermediate by-product in the form of an azeotropic or azeotrope-like composition of 1232zd and HF.

The azeotropic or azeotrope-like composition comprises, consists essentially of, or consists of, from about 1 to about 99 weight percent 1232zd, from about 2 to about 98 weight percent 1232zd, from about 20 to about 98 weight percent 1232zd, from about 15 to about 85 weight percent 1232zd, or from about 30 to about 55 weight percent 1232zd, based on the combined weight of the 1232zd and HF, and from 1 to about 99 weight percent HF, from about 2 to about 98 weight percent HF, from about 2 to about 80 weight percent HF, from about 15 to about 85 weight present HF, or from about 45 to about 70 weight percent HF, based on the combined weight of the 1232zd and HF.

The azeotropic or azeotrope-like composition of the present invention has a boiling point of about −10° C.±0.5° C. at a pressure of about 7 psia±1 psia. In one particular embodiment, an azeotropic or azeotrope-like composition of the present invention having 70±2 weight percent HF and 30±2 weight percent 1232zd has been found to boil at −10° C. and 7.1 psia.

The present disclosure also encompasses generating an azeotropic or azeotrope-like composition of 1232zd and HF followed by isolating the azeotrope from impurities. The present disclosure also includes steps for separating and purifying 1232zd from the azeotropic mixture, as discussed in greater detail below.

1232zd may be produced using one or more methods that are known in the art, in which 1232zd is produced as a component of a reactant mixture containing one or more impurities such as 1,1,1,3,3-pentachloropropane (240fa), 1,1,3,3-tetrachloro-1-fluoropropane (HFC-241fa), 1,3,3-trichloro-1,1-difluoropropane (242fa), 3,3-dichloro-1,1,1-trifluoropropane (243fa), (E)-1,3-dichloro-3,3-difluoroprop-1-ene (1231zd(E)), (Z)-1,3-dichloro-3,3-difluoroprop-1-ene (1231zd(Z)), (E)-1-chloro-3,3,3-trifluoropropene (1233zd (E)), (Z)-1-chloro-3,3,3-trifluoropropene (1233zd(Z)), 3-chloro-1,1,1,3-tetrafluoropropane (244fa), and 1,1,1,3,3-pentafluoropropane (245fa).

The first step in removing 1232zd from this mixture, or any other mixture containing 1232zd and an impurity, is by adding HF in an effective amount, as defined herein, to form an azeotropic composition of the 1232zd and HF, wherein the impurity itself does not form an azeotropic mixture with 1232zd, HF or a mixture of 1232zd and HF. Thereafter, the azeotropic composition is separated from the impurity using standard separation techniques, such as, but not limited to, liquid-liquid phase separation, distillation, scrubbing, or other art recognized separating means.

The purified azeotrope meets the need in the art for mixtures that have no ozone depletion potential and are negligible contributors to greenhouse global warming and are nonflammable. Such a mixture may be utilized in a wide range of uses such as, but not limited to, refrigerants, blowing agents, propellants and diluents for gaseous sterilization. The azeotrope may be provided in combination with other useful additives or ingredients for such purposes.

Post-purification, it also may be desirable to separate the component parts of the 1232zd and HF azeotrope to a purified form of 1232zd which is essentially HF-free. As used herein, "essentially HF-free" or "HF-free" refers to compositions of 1232zd which include less than 1.0 wt. % HF, less than 0.5 wt. % HF, or less than 0.1 wt. % HF.

Separation methods may include any method generally known in the art. In one embodiment, for example, the excess HF can be removed from the 1232zd by liquid-liquid phase separation, though other alternatives include distillation or scrubbing. The remaining HF can then be removed from the 1232zd by distillation and/or the use of one or more drying media or desiccants such as molecular sieves, calcium sulfate, silica, alumina, and combinations thereof.

Purified 1232zd may be used as an end product such as a refrigerant, blowing agent, propellant, or diluent for gaseous sterilization, or it may be used as a starting material, an intermediate, a monomer, or otherwise further processed for the production of alternative HFOs or similar compounds.

In another embodiment of the invention, the azeotrope-like compositions described herein can be used as a solvent, particularly a cleaning solvent. In certain embodiments, the solvent is contacted with an oxidized surface of a metal substrate to remove or reduce at least a portion of the oxidized surface. Such solvents may be applied to the targeted substrate via any means known in the art, such as dipping, spraying, wiping, and the like.

In certain embodiments, a sprayable composition is provided, including the novel azeotrope-like compositions described herein. In certain embodiments, the sprayable composition is an aerosol. In certain embodiments, the sprayable composition further includes other components such as inert ingredients, co-solvents, propellants, co-propellants, and the like.

In certain embodiments, the novel azeotrope-like compositions described herein are useful intermediates derived during synthesis of certain hydrochlorofluoroolefins, hydrofluoroolefins, and hydrofluorocarbons such as 1-chloro-3,3,3-trifluoropropene (HCFO-1233zd), 1,3,3,3-tetrafluoropropene (HFO-1234ze), and 1,1,1,3,3-pentafluoropropane (HFC-245fa). For example, where 1232zd and HF are introduced into a reactor during a synthesis reaction to produce 1-chloro-3,3,3-trifluoropropene (HCFO-1233zd), 1,3,3,3-tetrafluoropropene (HFO-1234ze), or 1,1,1,3,3-pentafluoropropane (HFC-245fa), at least a portion of these components form an azeotrope which subsequently can be recovered from the associated reaction product stream.

In certain embodiments, a method for reducing the boiling point of a hydrochloropropane is provided wherein the method comprises blending effective amounts of 1232zd and HF to form an azeotrope-like mixture consisting essentially of 1232zd and HF. Lowering the boiling point of 1232zd is advantageous when the 1232zd is used as a reactant in a vapor phase fluorination reaction. More particularly, lowering the boiling point facilitates vaporization of the compound and, thus, helps prevent decomposition of the compound and also reduces the amount of energy required by the fluorination process.

Accordingly, also provided is a method for fluorinating an organic compound including the steps of: (a) providing an azeotrope-like composition consisting essentially of 1232zd and HF; and (b) reacting at least a portion of said 1232zd in the vapor phase with a fluorinating agent to produce at least one fluorinated organic compound such as a pentafluoropropane, for example, 1,1,1,3,3-pentafluoropropane (HFC-245fa), a hydrochlorotrifluoropropene, for example, 1-chloro-3,3,3-trifluoropropene (HCFO-1233zd(E) and/or (Z)), and/or a tetrafluoropropene, for example, 1,3,3,3-tetrafluoropropene (HFO-1234ze).

The following non-limiting Examples serve to illustrate the invention.

Example 1

7.2 g of 1,3-dichloro-3,3-difluoroprop-1-ene (HCFO-1232zd) were combined with 13.4 g of HF to form a heterogeneous azeotrope mixture (by visual observation) at −10° C. and at 7.1 psia. The liquid composition of the bottom phase (the 1232zd rich layer) was also sampled and analyzed, and found to have HF present at 1.2 wt. % and 1232zd present at 98.8 wt. %.

Example 2

Binary compositions containing solely 1232zd and HF were blended to form heterogeneous azeotrope mixtures at different compositions. The vapor pressures of the mixtures were measured at −10° C., and the results are shown in Table 1 below, which shows the vapor pressure measurements of 1232zd and HF as a function of composition of weight percent HF at a constant temperature of about −10° C.

TABLE 1

Vapor pressure of 1232zd/HF compositions at −10° C.

| Wt. % HF | P (psia) |
|---|---|
| 0.0 | 0.7 |
| 5.9 | 5.8 |
| 16.1 | 6.4 |
| 24.8 | 6.7 |
| 35.0 | 7.1 |
| 44.7 | 7.7 |
| 45.7 | 7.8 |
| 62.1 | 7.2 |
| 72.5 | 6.5 |
| 85.2 | 5.8 |
| 95.1 | 5.0 |
| 100.0 | 4.7 |

The data also show that the mixture is an azeotrope since the vapor pressures of mixtures of 1232zd and HF are higher, at all indicated blend proportions, than those of 1232zd and HF alone, for example as indicated in the first and last rows when HF is 0.0 wt. % (and 1232zd is 100.0 wt. %) and when HF is 100.0 wt. % (and 1232zd is 0.0 wt. %). The data from Table 1 is also shown in graphic form in FIG. 1.

Example 3

The azeotropic composition of 1232zd and HF was also formed and then verified by Vapor-Liquid-Liquid Equilibrium (VLLE) experiment. 12.0 g of 1232zd were combined with 14.3 g of HF to form a heterogeneous mixture (by visual observation) at −10° C. The vapor compositions of the mixture were sampled at a temperature of −10° C. and a pressure of 7.1 psia, and the result indicated that the azeotropic composition is about 70±2 wt. % HF at −10° C., and the mixture was observed to be a heterogeneous azeotrope at a temperature of −10° C. and a pressure of 7.1 psia.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

The invention claimed is:

1. An azeotropic or azeotrope-like composition consisting of 1,3-dichloro-3,3-difluoroprop-1-ene (HCFO-1232zd) and hydrogen fluoride (HF).

2. The composition of claim 1, wherein the composition consists of from about 1 to about 99 wt. % hydrogen fluoride (HF) and from about 1 to about 99 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd).

3. The composition of claim 1, wherein the composition consists of from about 2 to about 99 wt. % hydrogen fluoride (HF) and from about 1 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd).

4. The composition of claim 1, wherein the composition consists of from about 2 to about 80 wt. % hydrogen fluoride (HF) and from about 20 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd).

5. The composition of claim 1, wherein the composition has a boiling point of about −10° C.±0.5° C. at a pressure of about 7 psia±1 psia.

6. A method of forming an azeotropic or azeotrope-like composition comprising forming a blend consisting essentially of from about 1 to about 99 wt. % hydrogen fluoride (HF) and from about 1 to about 99 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd).

7. The method of claim 6, wherein said forming step comprises forming a blend consisting of from about 2 to about 99 wt. % hydrogen fluoride (HF) and from about 1 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd).

8. The method of claim 6, wherein said forming step comprises forming a blend consisting of from about 2 to about 80 wt. % hydrogen fluoride (HF) and from about 20 to about 98 wt. % 1,3-dichloro-3,3-difluoroprop-1-ene (HCFO-1232zd), based on the combined weight of the hydrogen fluoride (HF) and 1,3-dichloro-3,3-difluoroprop-1-ene (HCFO-1232zd).

9. The method of claim 6, wherein the composition has a boiling point of about −10° C.±0.5° C. at a pressure of about 7 psia±1 psia.

10. A method for fluorinating an organic compound comprising:
    providing an azeotropic or azeotrope-like composition consisting of 1,3-dichloro-3,3-difluoroprop-1-ene (HCFO-1232zd) and hydrogen fluoride (HF); and
    reacting at least a portion of said 1,3-dichloro-3,3-difluoroprop-1-ene (HCFO-1232zd) in the vapor phase with a fluorinating agent to produce at least one fluorinated organic compound.

11. The method of claim 10, wherein said reacting step further comprises reacting at least a portion of said 1,3- dichloro-3,3-difluoroprop-1-ene (HCFO-1232zd) in the vapor phase with a fluorinating agent to produce 1-chloro-3,3,3-trifluoropropene (HCFO-1233zd).

12. The method of claim 10, wherein said reacting step further comprises reacting at least a portion of said 1,3-dichloro-3,3-difluoroprop-1-ene (HCFO-1232zd) in the vapor phase with a fluorinating agent to produce 1,1,1,3,3,-pentafluoropropane (HFC-245fa).

13. The method of claim 10, wherein said reacting step further comprises reacting at least a portion of said 1,3-dichloro-3,3-difluoroprop-1-ene (HCFO-1232zd) in the vapor phase with a fluorinating agent to produce 1,3,3,3-tetrafluoropropene (HFO-1234ze).

* * * * *